United States Patent
Goldstein

(10) Patent No.: US 11,589,329 B1
(45) Date of Patent: Feb. 21, 2023

(54) INFORMATION PROCESSING USING A POPULATION OF DATA ACQUISITION DEVICES

(71) Applicant: Staton Techiya LLC, Lighthouse Point, FL (US)

(72) Inventor: Steven W. Goldstein, Delray Beach, FL (US)

(73) Assignee: Staton Techiya LLC, Delray Beach, FL (US)

(*) Notice: Subject to any disclaimer, the term of this patent is extended or adjusted under 35 U.S.C. 154(b) by 0 days.

(21) Appl. No.: 17/235,130

(22) Filed: Apr. 20, 2021

Related U.S. Application Data

(63) Continuation of application No. 16/736,820, filed on Jan. 8, 2020, now Pat. No. 10,986,604, which is a
(Continued)

(51) Int. Cl.
*H04W 64/00* (2009.01)
*G16H 40/63* (2018.01)
(Continued)

(52) U.S. Cl.
CPC .......... *H04W 64/00* (2013.01); *G16H 40/63* (2018.01); *G16H 50/80* (2018.01);
(Continued)

(58) Field of Classification Search
CPC .......... H04W 64/00; H04W 84/02; H04J 3/26
See application file for complete search history.

(56) References Cited

U.S. PATENT DOCUMENTS

| 3,876,843 A | 4/1975 | Moen |
| 4,054,749 A | 10/1977 | Suzuki et al. |

(Continued)

FOREIGN PATENT DOCUMENTS

| EP | 1385324 | 1/2004 |
| EP | 1401240 | 3/2004 |

(Continued)

OTHER PUBLICATIONS

*Samsung Electronics Co., Ltd.*, and *Samsung Electronics, America, Inc.*, v. *Staton Techiya, LLC*, IPR2022-00282, Dec. 21, 2021.
(Continued)

*Primary Examiner* — Myron Wyche
(74) *Attorney, Agent, or Firm* — Akerman LLP; Peter A. Chiabotti

(57) ABSTRACT

Distributed systems, controllers and methods for processing information from a plurality of devices are provided. A distributed system includes a plurality of devices distributed in an environment. Each device has at least a communication capability for interchanging information with others of the devices and/or with a communication system. Each of at least some of the devices has one or more sensors for acquiring sensor data related to the environment proximate to the device. At least one of the communication system or one or more of the devices is configured as a controller configured to: select a subset of devices from among the plurality of devices, receive information based on the acquired sensor data of the selected subset, and combine the received information from the selected subset to determine a characteristic of the environment proximate to one or more of the devices.

11 Claims, 4 Drawing Sheets

Related U.S. Application Data continuation of application No. 16/055,488, filed on Aug. 6, 2018, now Pat. No. 10,602,474, which is a continuation of application No. 13/976,636, filed as application No. PCT/US2011/068103 on Dec. 30, 2011, now Pat. No. 10,045,321.

(60) Provisional application No. 61/431,507, filed on Jan. 11, 2011, provisional application No. 61/428,369, filed on Dec. 30, 2010.

(51) Int. Cl.
  *G16H 50/80* (2018.01)
  *G06F 11/30* (2006.01)
  *H04M 1/72403* (2021.01)

(52) U.S. Cl.
  CPC ...... *G06F 11/3013* (2013.01); *G06F 11/3058* (2013.01); *H04M 1/72403* (2021.01); *H04M 2250/12* (2013.01)

(56) References Cited

U.S. PATENT DOCUMENTS

| | | | |
|---|---|---|---|
| 4,088,849 A | 5/1978 | Usami et al. |
| 4,947,440 A | 8/1990 | Bateman et al. |
| 5,208,867 A | 5/1993 | Stites, III |
| 5,267,321 A | 11/1993 | Langberg |
| 5,317,273 A | 5/1994 | Hanson |
| 5,327,506 A | 7/1994 | Stites |
| 5,524,056 A | 6/1996 | Killion et al. |
| 5,577,511 A | 11/1996 | Killion |
| 5,903,868 A | 5/1999 | Yuen et al. |
| 5,923,624 A | 7/1999 | Groeger |
| 5,933,510 A | 8/1999 | Bryant |
| 5,946,050 A | 8/1999 | Wolff |
| 6,005,525 A | 12/1999 | Kivela |
| 6,021,207 A | 2/2000 | Puthuff et al. |
| 6,021,325 A | 2/2000 | Hall |
| 6,056,698 A | 5/2000 | Lseberg |
| 6,118,877 A | 9/2000 | Lindemann |
| 6,163,338 A | 12/2000 | Johnson et al. |
| 6,163,508 A | 12/2000 | Kim et al. |
| 6,226,389 B1 | 5/2001 | Lemelson et al. |
| 6,298,323 B1 | 10/2001 | Kaemmerer |
| 6,359,993 B2 | 3/2002 | Brimhall |
| 6,400,652 B1 | 6/2002 | Goldberg et al. |
| 6,415,034 B1 | 7/2002 | Hietanen |
| 6,493,204 B1 | 12/2002 | Glidden et al. |
| 6,567,524 B1 | 5/2003 | Svean et al. |
| 6,606,598 B1 | 8/2003 | Holthouse |
| 6,639,987 B2 | 10/2003 | McIntosh |
| RE38,351 E | 12/2003 | Iseberg et al. |
| 6,661,901 B1 | 12/2003 | Svean et al. |
| 6,728,385 B2 | 4/2004 | Kvaloy et al. |
| 6,748,238 B1 | 6/2004 | Lau |
| 6,750,295 B2 | 6/2004 | Albano |
| 6,754,359 B1 | 6/2004 | Svean et al. |
| 6,804,638 B2 | 10/2004 | Fiedler |
| 6,804,643 B1 | 10/2004 | Kiss |
| 7,039,195 B1 | 5/2006 | Svean |
| 7,039,585 B2 | 5/2006 | Wilmot |
| 7,050,592 B1 | 5/2006 | Iseberg |
| 7,072,482 B2 | 7/2006 | Van Doorn et al. |
| 7,107,109 B1 | 9/2006 | Nathan et al. |
| 7,158,933 B2 | 1/2007 | Balan |
| 7,177,433 B2 | 2/2007 | Sibbald |
| 7,209,569 B2 | 4/2007 | Boesen |
| 7,280,849 B1 | 10/2007 | Bailey |
| 7,430,299 B2 | 9/2008 | Armstrong et al. |
| 7,433,714 B2 | 10/2008 | Howard et al. |
| 7,450,730 B2 | 11/2008 | Berg et al. |
| 7,464,029 B2 | 12/2008 | Visser |
| 7,477,756 B2 | 1/2009 | Wickstrom et al. |
| 7,562,020 B2 | 6/2009 | Le et al. |
| 7,574,917 B2 | 8/2009 | Von Dach |
| 7,756,285 B2 | 7/2010 | Sjursen et al. |
| 7,778,434 B2 | 8/2010 | Juneau et al. |
| 7,903,825 B1 | 3/2011 | Melanson |
| 7,903,826 B2 | 3/2011 | Boersma |
| 7,920,557 B2 | 4/2011 | Moote |
| 7,944,775 B2 | 5/2011 | Sugiyama |
| 7,983,907 B2 | 7/2011 | Visser |
| 8,014,553 B2 | 9/2011 | Radivojevic et al. |
| 3,045,840 A1 | 10/2011 | Murata |
| 8,045,840 B2 | 10/2011 | Murata et al. |
| 8,086,093 B2 | 12/2011 | Stuckman |
| 8,140,325 B2 | 3/2012 | Kanevsky |
| 8,150,044 B2 | 4/2012 | Goldstein |
| 8,160,261 B2 | 4/2012 | Schulein |
| 8,160,273 B2 | 4/2012 | Visser |
| 8,162,846 B2 | 4/2012 | Epley |
| 8,218,784 B2 | 7/2012 | Schulein |
| 8,233,353 B2 | 7/2012 | Zhang et al. |
| 8,254,591 B2 | 8/2012 | Goldstein |
| 8,401,200 B2 | 3/2013 | Tiscareno |
| 8,493,204 B2 | 7/2013 | Wong et al. |
| 8,577,062 B2 | 11/2013 | Goldstein |
| 8,611,560 B2 | 12/2013 | Goldstein |
| 8,625,818 B2 | 1/2014 | Goldtsein |
| 8,718,305 B2 | 5/2014 | Usher |
| 8,750,295 B2 | 6/2014 | Liron |
| 8,774,433 B2 | 7/2014 | Goldstein |
| 8,798,278 B2 | 8/2014 | Isabelle |
| 8,855,343 B2 | 10/2014 | Usher |
| 8,917,894 B2 | 12/2014 | Goldstein |
| 8,983,081 B2 | 3/2015 | Bayley |
| 8,983,089 B1 | 3/2015 | Chu et al. |
| 9,037,458 B2 | 5/2015 | Park et al. |
| 9,053,697 B2 | 6/2015 | Park |
| 9,123,343 B2 | 9/2015 | Kurki-Suonio |
| 9,135,797 B2 | 9/2015 | Couper et al. |
| 9,191,740 B2 | 11/2015 | McIntosh |
| 9,196,247 B2 | 11/2015 | Harada |
| 9,336,767 B1 | 5/2016 | Barton et al. |
| 9,491,542 B2 | 11/2016 | Usher |
| 9,628,896 B2 | 4/2017 | Lchimura |
| 9,823,893 B2 | 11/2017 | Bhat et al. |
| 9,973,848 B2 | 5/2018 | Chhetri et al. |
| RE47,049 E | 9/2018 | Zhu et al. |
| 10,154,361 B2 | 12/2018 | Tammi et al. |
| 10,726,835 B2 | 7/2020 | Chua et al. |
| RE48,371 E | 12/2020 | Zhu |
| 2001/0046304 A1 | 11/2001 | Rast |
| 2002/0076057 A1 | 6/2002 | Voix |
| 2002/0098878 A1 | 7/2002 | Mooney |
| 2002/0106091 A1 | 8/2002 | Furst et al. |
| 2002/0118798 A1 | 8/2002 | Langhart et al. |
| 2002/0165719 A1 | 11/2002 | Wang |
| 2003/0007648 A1 | 1/2003 | Currell |
| 2003/0130016 A1 | 7/2003 | Matsuura |
| 2003/0152359 A1 | 8/2003 | Kim |
| 2003/0161097 A1 | 8/2003 | Le et al. |
| 2003/0165246 A1 | 9/2003 | Kvaloy et al. |
| 2003/0165319 A1 | 9/2003 | Barber |
| 2003/0198359 A1 | 10/2003 | Killion |
| 2004/0042103 A1 | 3/2004 | Mayer |
| 2004/0086138 A1 | 5/2004 | Kuth |
| 2004/0109668 A1 | 6/2004 | Stuckman |
| 2004/0109579 A1 | 7/2004 | Izuchi |
| 2004/0125965 A1 | 7/2004 | Alberth, Jr. et al. |
| 2004/0190737 A1 | 9/2004 | Kuhnel et al. |
| 2004/0196992 A1 | 10/2004 | Ryan |
| 2004/0203351 A1 | 10/2004 | Shearer et al. |
| 2004/0264938 A1 | 12/2004 | Felder |
| 2005/0028212 A1 | 2/2005 | Laronne |
| 2005/0058313 A1 | 3/2005 | Victorian |
| 2005/0068171 A1 | 3/2005 | Kelliher |
| 2005/0078838 A1 | 4/2005 | Simon |
| 2005/0123146 A1 | 6/2005 | Voix et al. |
| 2005/0207605 A1 | 9/2005 | Dehe |
| 2005/0281423 A1 | 12/2005 | Armstrong |
| 2005/0288057 A1 | 12/2005 | Lai et al. |
| 2006/0067551 A1 | 3/2006 | Cartwright et al. |

(56) References Cited

U.S. PATENT DOCUMENTS

| | | |
|---|---|---|
| 2006/0083390 A1 | 4/2006 | Kaderavek |
| 2006/0083395 A1 | 4/2006 | Allen et al. |
| 2006/0092043 A1 | 5/2006 | Lagassey |
| 2006/0140425 A1 | 6/2006 | Berg |
| 2006/0167687 A1 | 7/2006 | Kates |
| 2006/0173563 A1 | 8/2006 | Borovitski |
| 2006/0182287 A1 | 8/2006 | Schulein |
| 2006/0188075 A1 | 8/2006 | Peterson |
| 2006/0188105 A1 | 8/2006 | Baskerville |
| 2006/0195322 A1 | 8/2006 | Broussard et al. |
| 2006/0204014 A1 | 9/2006 | Isenberg et al. |
| 2006/0264176 A1 | 11/2006 | Hong |
| 2006/0287014 A1 | 12/2006 | Matsuura |
| 2007/0003090 A1 | 1/2007 | Anderson |
| 2007/0036377 A1 | 2/2007 | Stirnemann |
| 2007/0043563 A1 | 2/2007 | Comerford et al. |
| 2007/0086600 A1 | 4/2007 | Boesen |
| 2007/0143820 A1 | 6/2007 | Pawlowski |
| 2007/0189544 A1 | 8/2007 | Rosenberg |
| 2007/0255435 A1 | 11/2007 | Cohen |
| 2007/0291953 A1 | 12/2007 | Ngia et al. |
| 2008/0037801 A1 | 2/2008 | Alves et al. |
| 2008/0137873 A1 | 6/2008 | Goldstein |
| 2008/0145032 A1 | 6/2008 | Lindroos |
| 2008/0165988 A1 | 7/2008 | Terlizzi et al. |
| 2009/0010456 A1 | 1/2009 | Goldstein et al. |
| 2009/0024234 A1 | 1/2009 | Archibald |
| 2009/0076821 A1 | 3/2009 | Brenner |
| 2009/0085873 A1* | 4/2009 | Betts .............. H04R 3/005 345/169 |
| 2009/0122996 A1 | 5/2009 | Klein |
| 2009/0286515 A1 | 5/2009 | Othmer |
| 2010/0061564 A1 | 3/2010 | Clemow et al. |
| 2010/0296668 A1 | 11/2010 | Lee et al. |
| 2010/0316033 A1* | 12/2010 | Atwal .............. H04W 74/002 370/338 |
| 2011/0055256 A1 | 3/2011 | Phillips |
| 2011/0096939 A1 | 4/2011 | Ichimura |
| 2011/0116643 A1 | 5/2011 | Fiscareno |
| 2011/0264447 A1 | 10/2011 | Visser et al. |
| 2011/0293103 A1 | 12/2011 | Park et al. |
| 2014/0023203 A1 | 1/2014 | Rotschild |
| 2014/0122092 A1 | 5/2014 | Goldstein |
| 2014/0163976 A1 | 6/2014 | Park |
| 2015/0215701 A1 | 7/2015 | Usher |
| 2016/0104452 A1 | 4/2016 | Guan et al. |
| 2017/0155756 A1 | 6/2017 | Kim et al. |

FOREIGN PATENT DOCUMENTS

| | | |
|---|---|---|
| EP | 1519625 A2 | 3/2005 |
| JP | H0877468 | 3/1996 |
| JP | H10162283 | 6/1998 |
| WO | 2004114722 | 12/2004 |
| WO | 2006037156 A1 | 4/2006 |
| WO | 2006054698 | 5/2006 |
| WO | 2007092660 | 8/2007 |
| WO | 2008050583 | 5/2008 |
| WO | 2009023784 | 2/2009 |
| WO | 2012097150 | 7/2012 |

OTHER PUBLICATIONS

*Samsung Electronics Co., Ltd., and Samsung Electronics, America, Inc., v. Staton Techiya, LLC*, IPR2022-00242, Dec. 23, 2021.
*Samsung Electronics Co., Ltd., and Samsung Electronics, America, Inc., v. Staton Techiya, LLC*, IPR2022-00243, Dec. 23, 2021.
*Samsung Electronics Co., Ltd., and Samsung Electronics, America, Inc., v. Staton Techiya, LLC*, IPR2022-00234, Dec. 21, 2021.
*Samsung Electronics Co., Ltd., and Samsung Electronics, America, Inc., v. Staton Techiya, LLC*, IPR2022-00253, Jan. 18, 2022.
*Samsung Electronics Co., Ltd., and Samsung Electronics, America, Inc., v. Staton Techiya, LLC*, IPR2022-00324, Jan. 13, 2022.
*Samsung Electronics Co., Ltd., and Samsung Electronics, America, Inc., v. Staton Techiya, LLC*, IPR2022-00281, Jan. 18, 2022.
*Samsung Electronics Co., Ltd., and Samsung Electronics, America, Inc., v. Staton Techiya, LLC*, IPR2022-00302, Jan. 13, 2022.
*Samsung Electronics Co., Ltd., and Samsung Electronics, America, Inc., v. Staton Techiya, LLC*, IPR2022-00369, Feb. 18, 2022.
*Samsung Electronics Co., Ltd., and Samsung Electronics, America, Inc., v. Staton Techiya, LLC*, IPR2022-00388, Feb. 18, 2022.
*Samsung Electronics Co., Ltd., and Samsung Electronics, America, Inc., v. Staton Techiya, LLC*, IPR2022-00410, Feb. 18, 2022.
*Samsung Electronics Co., Ltd., and Samsung Electronics, America, Inc., v. Staton Techiya, LLC*, IPR2022-01078, Jun. 9, 2022.
*Samsung Electronics Co., Ltd., and Samsung Electronics, America, Inc., v. Staton Techiya, LLC*, IPR2022-01099, Jun. 9, 2022.
*Samsung Electronics Co., Ltd., and Samsung Electronics, America, Inc., v. Staton Techiya, LLC*, IPR2022-01106, Jun. 9, 2022.
*Samsung Electronics Co., Ltd., and Samsung Electronics, America, Inc., v. Staton Techiya, LLC*, IPR2022-01098, Jun. 9, 2022.
Olwal, A. and Feiner S. Interaction Techniques Using Prosodic Features of Speech and Audio Localization. Proceedings of IUI 2005 (International Conference on Intelligent User Interfaces), San Diego, CA, Jan. 9-12, 2005, p. 284-286.
Bernard Widrow, John R. Glover Jr., John M. McCool, John Kaunitz, Charles S. Williams, Robert H. Hearn, James R. Zeidler, Eugene Dong Jr, and Robert C. Goodlin, Adaptive Noise Cancelling: Principles and Applications, Proceedings of the IEEE, vol. 63, No. 12, Dec. 1975.
Mauro Dentino, John M. McCool, and Bernard Widrow, Adaptive Filtering in the Frequency Domain, Proceedings of the IEEE, vol. 66, No. 12, Dec. 1978.

\* cited by examiner

INFORMATION PROCESSING USING A POPULATION OF DATA ACQUISITION DEVICES

CROSS-REFERENCE TO RELATED APPLICATION(S)

This application is a continuation of and claims priority to allowed U.S. patent application Ser. No. 16/736,820, filed 8 Jan. 2020, which is a continuation of and claims priority to allowed U.S. patent application Ser. No. 16/055,488, filed Aug. 6, 2018, which is a continuation of and claims priority to U.S. patent application Ser. No. 13/976,636, filed on Oct. 1, 2013, which is a National Stage Entry of PCT/US11/68103 filed on Dec. 30, 2011, which claims priority to and the benefit of U.S. Provisional Patent Application Ser. No. 61/431,507 filed Jan. 11, 2011, and which also claims priority to and the benefit of U.S. Provisional Patent Application Ser. No. 61/428,369 filed Dec. 30, 2010, all of which are herein incorporated by reference in their entireties.

FIELD OF THE INVENTION

The present invention relates to processing of information from a population of data acquisition devices, and in some examples, relates to processing of audio or multimedia data acquired from an adaptively selectable population of personal wireless devices.

BACKGROUND

Devices that are capable of acquiring, and in some cases locally processing, audio or multimedia information from their local environment have become ubiquitous over the past several years, and there is little reason to expect that such a trend will not continue. For example, "smart" cellular telephones (e.g., Apple iPhone.RTM., Android™-operating system based phones) have significant local processing capabilities as well as audio and video acquisition devices.

SUMMARY OF THE INVENTION

In one aspect of the present invention, in general, the audio and multimedia acquisition capabilities of a set of devices may be exploited to aggregate acquired content and fuse the information in that content, for instance, for audio scene analysis. In some example embodiments, devices from a large population may be adaptively selected and/or configured according to triggering events detected at the devices or by the network. Relating to the audio scene, the information sensed and acquired from one or more devices may be processed, customized and personalized to consumers to mitigate, amplify or pass-through acoustic and other information to users, based on factors such as models of users' requirements and users' past information consumption behavior. Thus an exemplary system of the present invention may mediate ambient and explicitly supplied information, especially audio information, and may act as an arbiter of information for the user. Some of the system actions may be based on information from one device, while other actions may be based on information from multiple devices. The information filtered to users may be utilized to form virtual communities based on shared interests and common information, and to ensure that relevant information including alerts, marketing information, and news reaches these communities.

According to another aspect of the present invention, in general, a distributed system may include a plurality of distributed devices, with at least one of a communication system or one or more of the distributed devices configured as a controller. Each device has at least a communication capability for interchanging information with other of the devices and/or with the communication system. At least one of the devices may include one or more sensors for acquiring sensor data related to the environment of the device. The controller is configured to perform functions including: determining locations of at least some of the devices, selecting devices from among the plurality of devices and receiving information based on the sensor data acquired at the selected devices, and combining the information received from multiple of the selected devices to determine one or more characteristics of the environment of one or more of the devices.

In other aspects of the present invention, the distributed system may include devices that mediate all audio information sensed at the device to mitigate, amplify or pass-through information. In some examples, such information is optionally logged and analyzed to determine trend-related information.

Other features and advantages of the invention are apparent from the following description, and from the claims.

BRIEF DESCRIPTION OF THE DRAWINGS

The invention may be understood from the following detailed description when read in connection with the accompanying drawing. It is emphasized, according to common practice, that various features of the drawings may not be drawn to scale. On the contrary, the dimensions of the various features may be arbitrarily expanded or reduced for clarity. Moreover, in the drawing, common numerical references are used to represent like features. Included in the drawing are the following figures.

DETAILED DESCRIPTION OF THE INVENTION

1 System Overview

Figure 1:
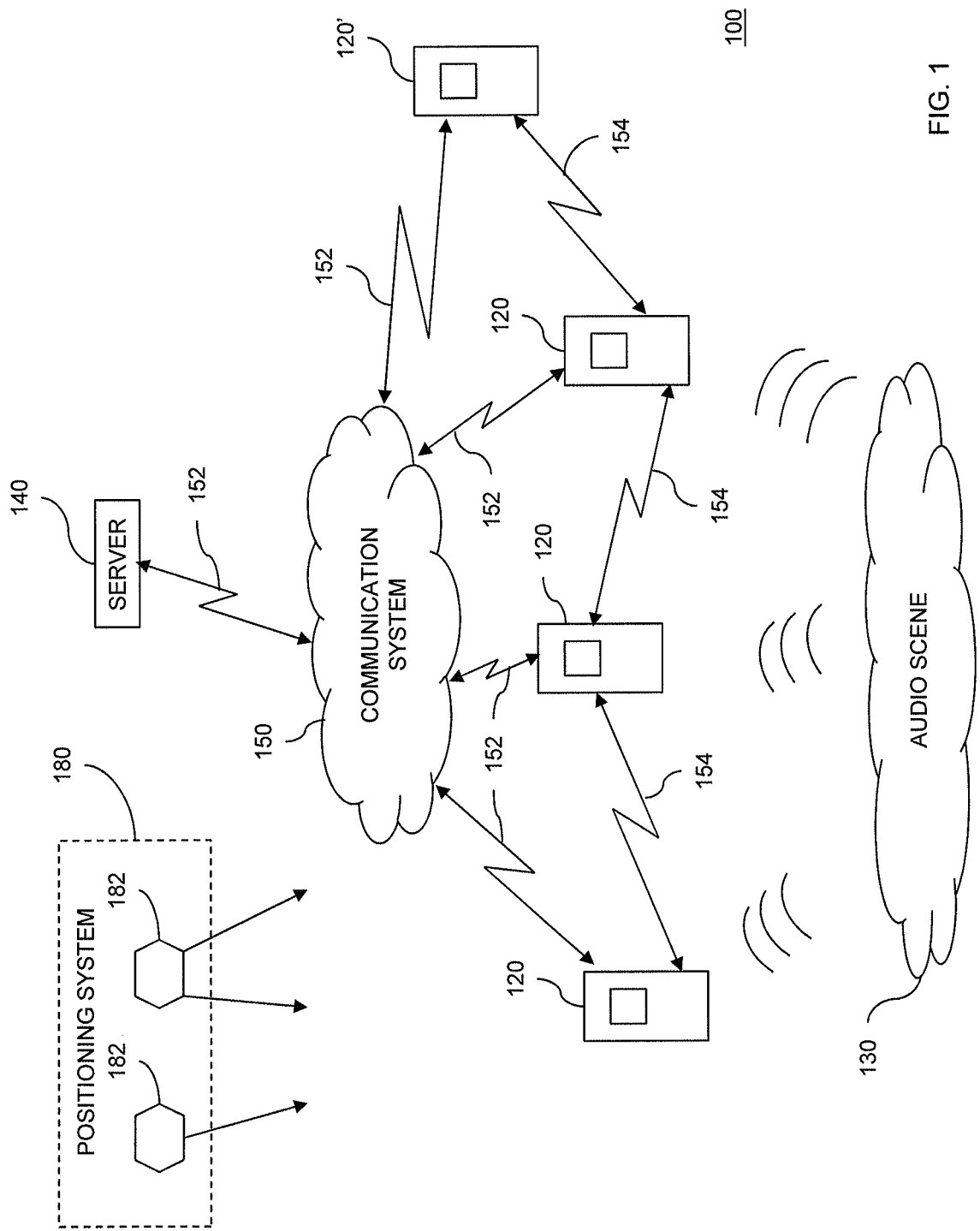
FIG. 1 is a functional block diagram of an information processing system, according to an exemplary embodiment of the present invention.

Personal wireless devices, as well as other types of computing or communication devices, have become ubiquitous in our environment. Generally, such devices have a number of sensors, which may include, for instance, microphones, cameras, accelerometers, and in some cases may even have sensors for biometric information, such as heart rate. Such devices also generally include one or more communication systems, for example, a cellular telephone radio system (e.g., Code Division Multiple access (CDMA) or Global System for Mobile Communications (GSM)), a wireless local area network system (e.g., Wi-Fi, IEEE 802.11), wired computer network connections (e.g., data network connections via USB cradles, possibly via desktop computer applications) and in some cases other systems based on radio frequency (e.g., Bluetooth.RTM.) or optical (e.g., infra-red) transmission. Finally, such devices generally are "location aware" and/or locatable by the infrastructure in which they operate. For example, such devices may have global positioning system (GPS) receivers, enhanced GPS (which operates in conjunction with cellular telephone infrastructure), and/or Wi-Fi based maps (which use a map of Wi-Fi access points to locate the device). The cellular infrastructure may, for example, be able to locate the device based on cellular signal strength and/or triangulation approaches.

In some aspects of the present invention, the combination of characteristics of these devices provides a potentially rich source of information that may be combined in a way that generates valuable information that is not necessarily available to any individual device. As an illustrative example, audio processed locally at many different devices may be combined to identify geographic or social group trends based on keywords spoken or other acoustic events (e.g., coughs) that are detected at the devices.

Detection of coughs is an example where detection of non-speech acoustic events may be useful. Because a cough is often a sudden and often repetitively occurring reflex, frequent coughing may indicate the presence of a disease (e.g., many viruses and bacteria benefit evolutionarily by causing the host to cough, which helps to spread the disease to new hosts). Most of the time, coughing is caused by a respiratory tract infection but can be triggered by choking, smoking, air pollution, asthma, gastro-esophageal reflux disease, post-nasal drip, chronic bronchitis, lung tumors, heart failure and medications such as ACE inhibitors. Detection of such events in the vicinity of the devices may provide significant information.

In other aspects of the present invention, the rich sensor capabilities of the devices may provide a way to track activity of a user (e.g., owner) of the device, to enhance the user's experience with various computing applications (such as searching or personalization). As an illustrative example, topics of conversation in the vicinity of the device may affect the ranking of search results or the ordering of presentation of news stories on the device.

In some aspects of the present invention, the rich source of information over many devices and the tracking of individual activity may be combined, to benefit from their synergy.

Referring to FIG. 1, a functional block diagram of an exemplary information processing system, designated generally as system 100, is shown. System 100 may include one or more distributed devices 120 (also referred to herein as devices 120) and device 120' (also referred to as controller 120') in an environment. One or more of devices 120 and device 120' may be configured to acquire information relating to audio scene 130. Device 120' may be the same as device 120, except that device 120' may be configured to act as a controller for selectively acquiring sensor information from among devices 120 and for determining a characteristic of audio scene 130. Although one device 120' is illustrated as being a controller, it is understood that multiple devices 120' may act as controllers.

Although device 120' is illustrated as a controller for gathering sensor information and determining a characteristic of audio scene 130, it is understood that communication system 150 and/or server 140 may also be configured to act as a controller. Communication system 150 or server 140 may collect at least one of sensor information from devices 120, 120', local data analysis information from devices 120, 120' or scene analysis information from device 120'.

Devices 120 and device 120' may be capable of direct communication with each other, via communication link 154. Devices 120 and device 120' may also be capable of communication with communication system 150, via communication link 152. Devices 120 and device 120' may also be in communication with central server 140, via communication system 150 and communication link 152. Devices 120, 120' may include wired or wireless devices. As discussed further below, devices 120, 120' may be at fixed positions or may be mobile devices.

In one exemplary embodiment, a number of devices 120 are present in an environment. In some examples, the devices 120 (and device 120') are cellular telephones (e.g., "smartphones"). The environment represented by audio scene 130 may be an urban environment, for example, with the devices 120, 120' being present on city streets, in office buildings, or in homes of the users. Generally, the devices 120, 120' may be personal to the users/owners (of the devices), and may be mobile devices, carried with the user throughout the day.

In FIG. 1, a small number of representative devices 120, 120' are illustrated. As discussed further below, the potentially enabled devices 120, 120' may be part of a large population of devices (e.g., a large fraction of the telephones in a metropolitan area) and system 100 may adaptively enable particular subsets of the devices 120 and/or selectively configure enabled devices 120. For instance, device 120' (or server 140) may enable and/or configure the devices 120 according to triggering events detected at one or more devices 120, 120'.

It should be understood that the description below focuses on smartphones as an example, and other types of fixed or mobile devices may be used in conjunction with or instead of smartphones. Also, the description below focuses on aggregation or combination of audio information as an example, but aggregation and processing of other forms of information, including video and biometric information may be performed in conjunction with or instead of the audio data examples described below.

As introduced above, any particular device 120, 120' is able to sense some aspect of an overall audio "scene" in its environment. Such a scene may include, for example, the device owner's own speech even when not carrying out a telephone call, other sounds made by the owner (such as coughing), the speech of others in proximity to the user and environmental sounds in proximity to the user (such as sirens, gunshots, etc.).

Generally, system 100 makes use of the audio acquisition capabilities of one or more of the devices 120, 120' in order to extract information related to the views of the audio scene 130 by the one or more devices 120, 120'. In one exemplary approach to acquisition of the raw content, every device 120 could continually transmit its acquired signals over communication system 150 to a central server 140 (via communication link 152). For example, the communication system 150 may comprise a cellular telephone system and/or a wireless data network. However, such continual transmission may not be feasible due to the sheer volume given the large number of devices 120, 120' that are fielded, and may raise other issues regarding privacy of those in the environments of the devices 120, 120'.

Another exemplary approach to extracting information is for each device 120, 120' to perform a local signal analysis based on the signals acquired by that device. However, such an approach may have limitations due to the computational limitations of the devices 120, 120'. Also, a purely local processing may lose advantages that could be gained by fusing of information from multiple devices 120, 120'

An exemplary approach describe below addresses some of the limitations of a purely local or a purely centralized approach using a combination of one or more of the following features: [0028] 1) Local processing of acquired signals (on devices 120), at least to identify occurrences of events that may be of interest; [0029] 2) Local buffering of audio for selective transmission to device 120' or central server 140, for example, on an ongoing basis or based on a request from device 120' or server 140, or based on local identification of a local event (at one or more of devices 120); and [0030] 3) Selective enabling of acquisition and/or processing (or specification of the type of processing) at particular devices 120, 120', for example, based on their geographic location and/or other proximity metrics (e.g., a social network rather than a geographic distance metric).

Note that the locations of the devices 120, 120' (e.g., three-dimensional coordinates) are generally known by the devices 120, 120' and/or central server 140. As an example, a positioning system 180 makes use of units having known locations, such as GPS satellites 182, fixed cellular transmission towers, Wi-Fi access points, etc. to maintain an estimate of the positions of the devices.

Figure 2A:
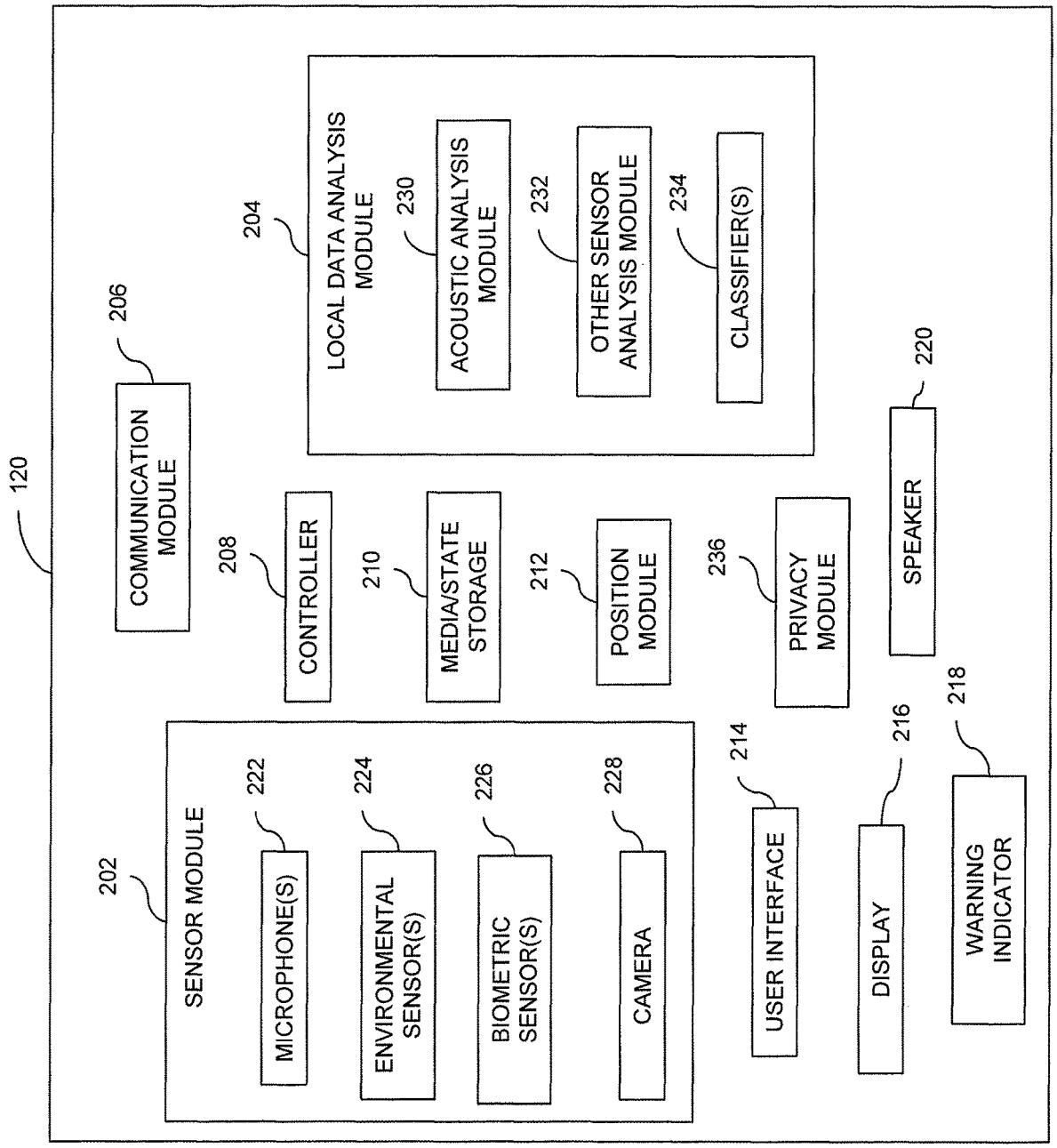
FIG. 2A is a functional block diagram of a distributed device of the system shown in FIG. 1, according to an exemplary embodiment of the present invention.

Referring to FIG. 2A, a functional block diagram of exemplary device 120 is shown. Device 120 may include one or more of sensor module 202, local data analysis module 204, communication module 206, controller 208, media/state storage 210, position module 212, user interface 214, display 216, warning indicator 218, speaker 220 and privacy module 236.

A typical device 120 includes communication module 206, which provides a communication link 152 through the communication system 150 to sever 140 and/or a communication link 154 to other devices 120, 120'. Communication module 206 may also serve a role in acquiring positioning signals (e.g., GPS signals, Wi-Fi signal strengths, etc.), and may also provide a way to communicate directly with other devices 120.

Device 120 may include sensor module 202 for the acquisition of sensor information. Sensor module 202 may include one or more microphones 222 for collecting acoustic information regarding audio scene 130 (FIG. 1). Sensor module 202 may also include one or more environmental sensors (such as a temperature sensor, a motion sensor such as an accelerometer) for collecting environmental information associated with device 120. Sensor module 202 may also include one or more biometric sensors 226 (such as heart rate) for sensing biometric information regarding a user of device 120. Sensor module 202 may also include camera 228 (i.e., an image sensor) for capturing still images and/or video of the surrounding environment of device 120. Sensor module 202 may also include a compass for providing location information. In general, sensor module 202 may include any sensor capable of measuring a physical quantity and converting it into a signal that may be used by system 100. For example, sensors in sensor module 202 may also include, without limitation, one or more of light detection sensors, proximity sensors, gravity detection sensors, a magnetic field detection sensors, electrical field detection sensors, vibration sensors, pressure sensors, humidity sensors, moisture sensors, toxin detection sensors, nutrient detection sensors or pheromone detection sensors.

User interface 214 may include any suitable user interface capable of providing parameters for one or more of sensor module 202, local data analysis module 204, communication module 206, media/state storage 210, position module 212, display 216, warning indicator 218, speaker 220 and privacy module 236. User interface 214 may include, for example, a pointing device, a keyboard and/or a display device.

Device 120 may include display 216, warning indicator 218 and/or speaker 220 for presenting information to a user of device 120. Display 216 may include any suitable display device capable of presenting information on device 120. Warning indicator 218 may include any suitable visual indicator for presenting a warning on device 120. The warning may include, for example, an indication that audio information is being recorded. It is understood that speaker 220 may also audibly present a warning indication. Although user interface 214 and display 216 are illustrated as separate devices, it is understood that the functions of user interface 214 and display 216 may be combined into one device. According to an exemplary embodiment, device 120 may receive acoustic and/or other information (via display 216, warning indicator 218 and/or speaker 220) that has been mitigated, amplified and/or passed to device 120 from device 120' (FIG. 1) based on information acquired from one or more devices 120.

Device 120 may include position module 212, to maintain a position estimate for device 120. For example, position module 212 may use positioning system 180 (FIG. 1) to obtain the position estimate.

Media/state storage 210 may store at least one of raw sensor information (from sensor module 202), locally analyzed information (from local data analysis module 204) or location information (from position module 212). Media/state storage 210 may include, for example, a magnetic disk, an optical disk, flash memory or a hard drive.

Controller 208 may be coupled, for example, via a data and control bus (not shown) to one or more of sensor module 202, local data analysis module 204, communication module 206, media/state storage 210, position module 212, user interface 214, display 216, warning indicator 218, speaker 220 and privacy module 236. Controller 208 may be configured to control acquisition of sensor information, local analysis of sensor information, transmission and/or receipt of sensor information, transmission and/or receipt of local analysis information, as well as any presentation of information by device 120 (such as via display 216, warning indicator 218 and/or speaker 220). Controller 208 may include, for example, a logic circuit, a digital signal processor or a microprocessor. It is understood that one or more functions of local data analysis module 204 may be performed by controller 208.

Local data analysis module 204 may be configured to analyze information collected locally by sensor module 202 for device 120. Local data analysis module 204 may include acoustic analysis module 230 for analyzing audio information (such as from one or more microphones 222). The audio information may include speech, music as well as environmental sounds (such as an approaching train). The speech may be generated by a user of device 120, as well as by other individuals proximate to device 120. Local data analysis module 204 may perform the analysis either locally or with the aid of backend server architecture or similar mechanisms.

Local data analysis module 204 may also include other sensor analysis module 232 for analyzing information from other sensors of sensor module 202. For example, other sensor analysis module 232 may analyze information from one or more of environmental sensor(s) 224, biometric sensor(s) 226 and/or camera 228. Local data analysis module 204 may combine results from acoustic analysis module 230 (such as keywords, target sounds) and other sensor analysis module 232 to determine the occurrence of one or more particular events (and/or a characteristic of audio scene 130).

Acoustic analysis module 230 and/or other sensor module 232 may also pre-process the respective sensor information, for example, to substantially remove or reduce noise. Modules 230, 232 may also filter the noise-reduced sensor information to identify high value signals which may be indicative of the occurrence of particular events.

Local data analysis module 230 may include classifiers 234 associated with acoustic analysis module and/or other sensor analysis module. Classifiers 234 may be used to build profiles of audio information, environmental information, biometric information and/or image information.

In an exemplary embodiment, acoustic analysis module 230 may preprocess the audio information to recognize speech, perform keyword spotting on speech information, and in addition build voice models of various speakers within the auditory range of the device. The models may, for example, use classifiers 234 and machine learning methods to identify gender, probable age range, nationality and other demographic features from the speech signals.

In addition, there may be classifiers 234, for instance, to recognize any slurring due to the influence of alcohol or similar substances, accent classifiers to detect and identify accent patterns belonging to specific language groups, and emotion classifiers to classify speakers and speech into happy, sad, stressed, angry or other emotional states. Thus, given any audio input that includes any speech, individual devices 120 or system 100 (FIG. 1) as a whole may be able to build an acoustic profile of each speech participant in that input, where the profile not only includes the keywords spotted, but also other data such as demographic data about each speaker including gender, probable age, possible nationality etc., as well as classifier results about emotional state, and/or whether the speaker is under the influence.

The acquisition of keywords with demographic data may help advertisers target their sales, based on factors such as gender, age and potential levels of disposable income, and to track their sale cycle from users noticing their advertisements to those users who actually make a purchase. Emotion indicators may be used to take palliative or preventative steps to avoid customer dissatisfaction. Other information like slurring may be used as corroboratory information in situations such as accidents or may be used to prevent accidents.

Privacy module 236 may include mechanisms to implement privacy and/or security requirements and policies for applications relating to the acquisition and use of information of various kinds, including audio information, by one or more devices associated with a number of carriers. These policies and mechanisms may control the use of devices 120 (and device 120' (FIG. 1)) including the ability to remotely switch on and switch off sensing (e.g., listening), the ownership of any audio information garnered by these devices 120 (and device 120' (FIG. 1)), the users' ability to easily control sensing and information acquisition, mechanisms to opt-in and opt-out of applications, carrier-wide or network-wide data gathering, the protection of any audio personally identifiable information (PII) that is gathered, and any aggregated data that is created from a number of devices 120 (device 120' (FIG. 1) and networks. Policies or standard practices may also be established for private or semi-private situations where not all users present have opted-in for data acquisition. For example, when system 100 (FIG. 1) records speech from users that are not likely to be opted-in to the information acquisition, system 100 may provide a warning indication to all devices 120 in the immediate vicinity to indicate that audio information is being recorded. The warning indication may be provided on warning indicator 218.

Figure 2B:
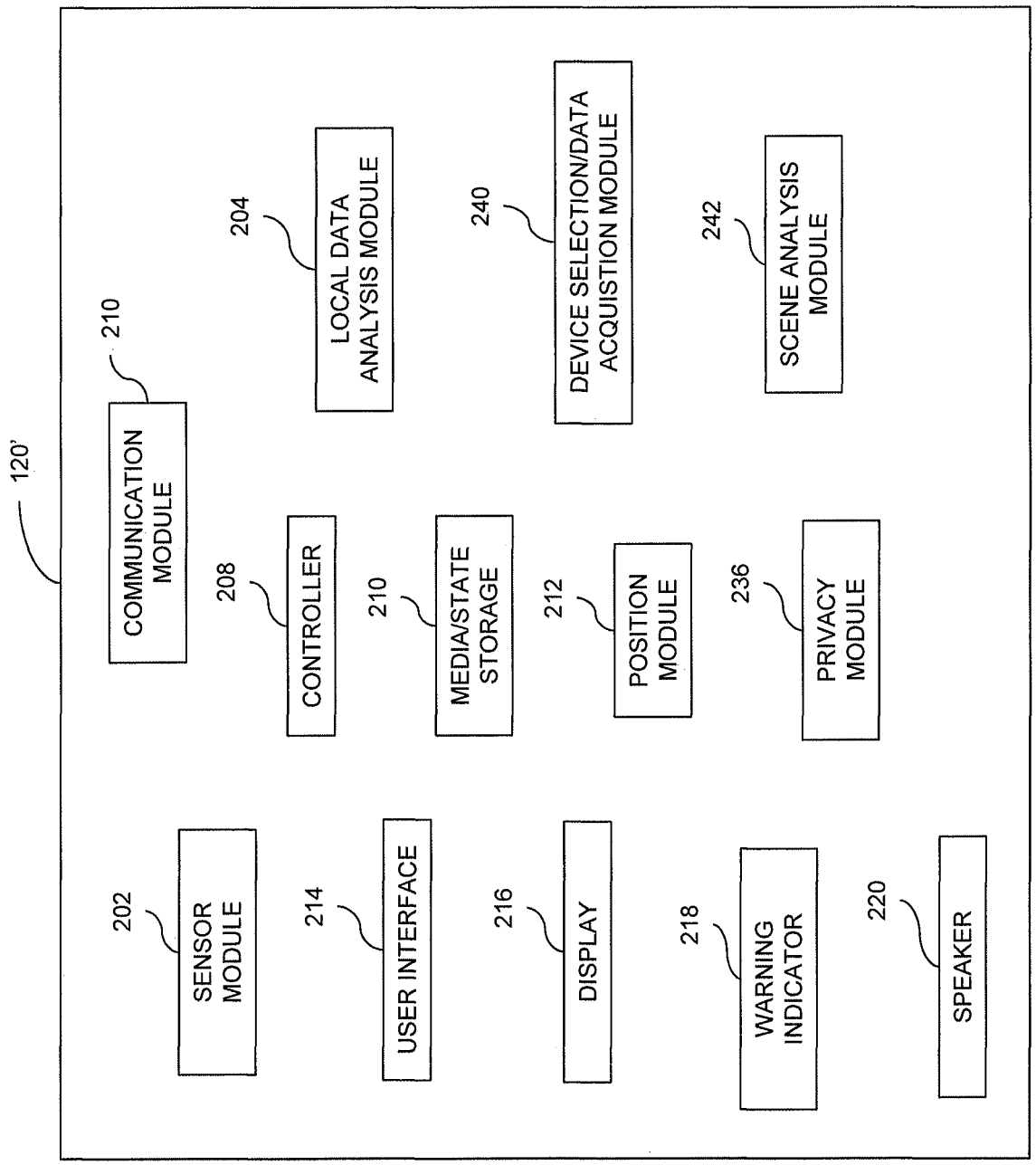
FIG. 2B is a functional block diagram of a controller of the system shown in FIG. 1, according to an exemplary embodiment of the present invention.

Referring next to FIG. 2B, a functional block diagram of exemplary device 120' is shown. Device 120' is similar to device 120 (FIG. 2A), except that device 120' may also include device selection/data acquisition module 240 and scene analysis module 242. Similarly to device 120 (FIG. 2A), components of device 120' may be coupled together via a data and control bus (not shown).

Device selection/data acquisition module 240 (also referred to herein as module 240) may receive sensor information and/or locally analyzed information from selected devices 120 (FIG. 1). Scene analysis module 242 may combine the sensor information and/or locally analyzed information from among the selected devices, in order to determine at least one characteristic of audio scene 130 (or the environment, in general).

Module 240 may determine the locations of at least some of devices 120 (FIG. 1). Module 240 may select one or more devices 120 (FIG. 1) from among plural devices 120, for example, based on the location of these devices 120 as well as any characteristics (such as an event) determined by scene analysis module 242. Accordingly, as a characteristic is detected (by scene analysis module 242), module 240 may adaptively acquire information from selected devices 120 (FIG. 1), in order to better analyze audio scene 130. Module 240 may also configure selected devices 120 (FIG. 1) to acquire specific information, (for example one device 120 may acquire image data via camera 228 (FIG. 2A) whereas another sensor may be configured to acquire audio data via microphone 222 (FIG. 2A). As another example, module 240 may configure multiple devices 120 to acquire audio data via respective microphones 222 (FIG. 2A), so that the multiple microphones 222 form a beam forming array.

Referring generally to FIGS. 1, 2A and 2B, system 100 makes use of one or more of enabling and configuring of devices (via device selection/data acquisition module 240) for prospective monitoring, access to logged data for retrospective analysis, and real-time notification of events (such as by scene analysis module 242). This adaptation of system 100 may be based on detection of triggering events at the devices 120, 120'. For example, device 120' may enable detection of certain acoustic events (e.g., words, spoken topics, music, and environmental sounds) and may adapt the configurations on selected devices 120 based on reports from other devices 120.

Device 120' (and devices 120) may include software for coordinating the set of devices 120. The software may have centralized control, peer-to-peer control or a hybrid model involving centralized, peer-to-peer and other control mechanisms. Individual devices 120, 120' may switch between being master devices controlling other devices, or slave devices under the temporary partial control of other devices. The network of devices 120, 120' may so configure itself to optimize power consumption on individual devices 120 by distributing the sensing load across a number of devices 120, 120', or by other mechanisms such as sharing bandwidth across devices 120, 120'. The networking used may be based on ideas related to mobile ad hoc networks (MANET), Scatternet or other mechanisms.

For example, system 100 may dynamically organize and reorganize its nodes into hierarchies or graphs, with some devices 120, 120' chosen to be master nodes while other possibly geographically proximate devices to be slave nodes. Slave nodes may perform actions based on instructions from master nodes. They may preprocess information and convey processed information to master nodes, instead of conveying all information acquired, thus distributing computation among nodes and reducing the communication bandwidth. In addition, communication requirements may improve because only a few master nodes may communicate with each other, instead of all, say N devices trying to communicate with each other, which would require (N.sup.2/2) connections.

Because each node knows its location, depending on system requirements, the network may organize itself into one or more linear chains or local groups, where information is passed between physically proximate devices, very much like a bucket brigade conveying information. With a peer-to-peer architecture, individual devices 120, 120'—either just master nodes or both master nodes and slave nodes—may record information about neighboring nodes and their capabilities and features, so that, for instance, connectivity between any pair of nodes can easily and effectively be established at low computational cost.

Other optimization techniques may also be adopted—for instance, when data logs are recorded, the system may determine if several devices are in the same audio or other sensor context. For example, if several phones 120, 120' are located in the same context, not every phone 120, 120' has to record all data—the system 100 may designate a scribe node which acts as a local repository for data and for ensuring the data gets stored to some centralized server 140 (or device 120') in the cloud. This may save considerable logging effort on the part of the other nodes.

Alternatively or in addition, the system 100 may distribute sensor load among devices 120, 120' so that not every node has to acquire information via all of its sensors in sensor module 202. Some sensor modules 202 may concentrate on acquiring audio information, while other devices 120, 120' may acquire position information and still other sensor modules 202 may acquire temperature or altitude information, and so on. This may reduce power and communication bandwidth requirements for the entire system 100. Several such schemes may be devised to optimize the throughput and efficiency of the system as a whole. According to an exemplary embodiment, system 100 may also distribute processing of sensor information among devices 120, 120', so that different individual tasks are performed by devices 120, 120'. This may reduce the computational burden on some devices 120 (or device 120') which may not have suitable processing capabilities for a specific task.

The system 100 as a whole may use carrier-agnostic handlers in the cloud. Specifically, the networking may utilize services from a number of wireless telephony, Wi-Fi or other carriers, and suitable policies may be put in place to enable carrier-agnostic behaviors. Specifically, so that no user may be denied sharing of information because of association with specific carriers, and so that digital bridges exist to share information across carriers where desired. In a variant, some features may be made unique to a carrier for marketing reasons.

It is understood that devices 120, 120' do not have to be phones. Devices 120, 120' may be stand-alone devices, or may be an integral part of a GPS, hearing aid, mobile phone, TV remote, car key fob, portable game controller or similar device. Device 120 (and/or device 120') may be carried by the user on his person, or be installed in or on a vehicle such as a car.

For certain applications, devices 120 (and/or device 120') may be fixed and installed at home, or be part of fixed telephones, desktop computers, TV sets or game consoles.

Each device 120 (and/or device 120') may include one or more sensors with associated software. Different kinds of devices 120, 120' may include different sensors and/or different software. If device 120 or device 120' is more like a smartphone, system 100 may have access to textual data including electronic mail, chat transcripts and documents, and audio data including phone conversations, music on the device or streamed to the device, ambient audio picked up by microphones, and user search logs. All of this data may be relevant to the user. This data, along with the user's context and environmental variables, may be used for personalization of information consumed by the user and then where appropriate repurposed for commercial applications to the user or the community at large.

Figure 3:
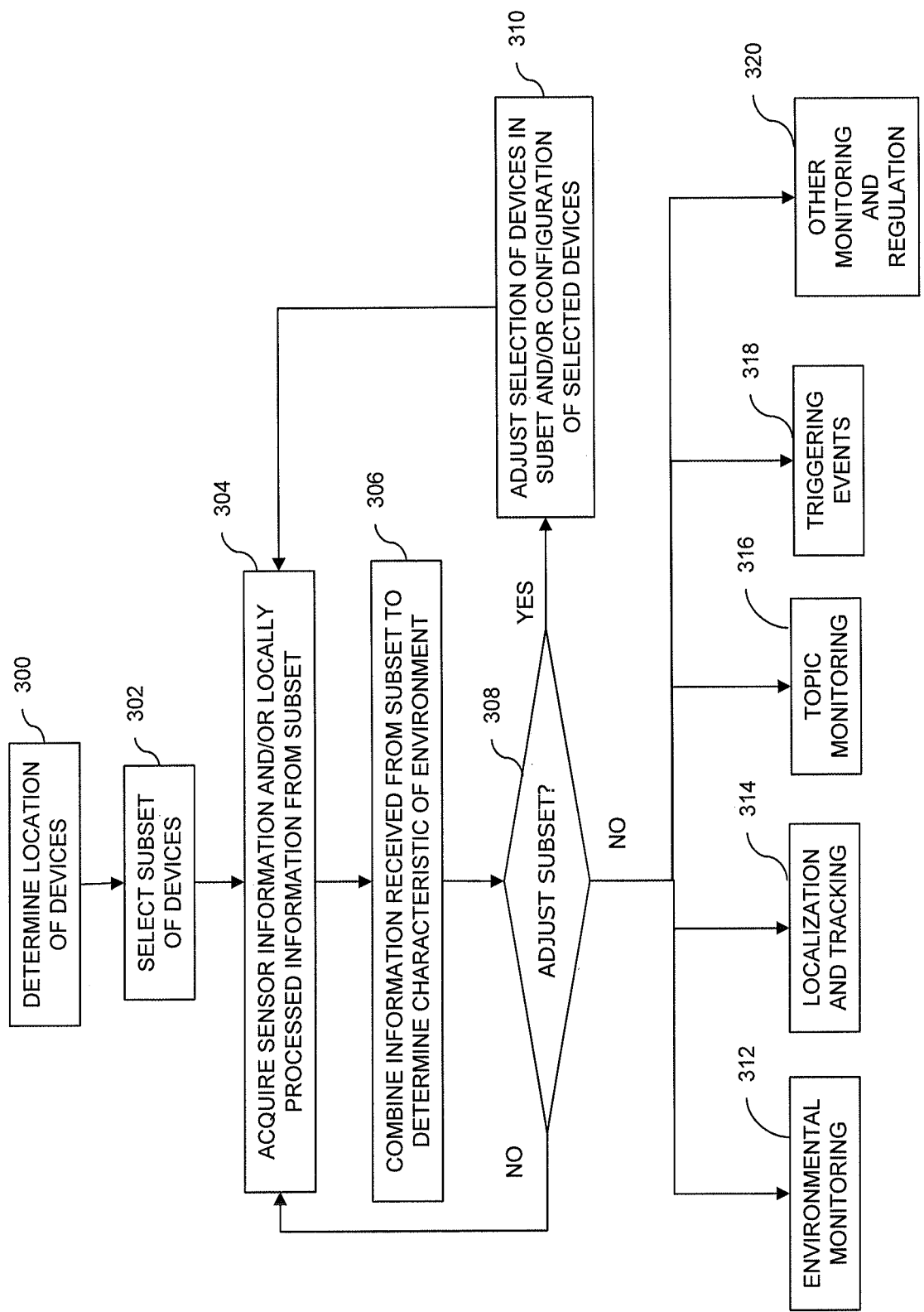
FIG. 3 is a flowchart diagram of an exemplary method for processing information from a plurality of distributed devices, according to an exemplary embodiment of the present invention.

Referring to FIG. 3, a flowchart diagram of an exemplary method for processing information from a plurality of distributed devices is shown. The steps illustrated in FIG. 3 represent an example embodiment of the present invention. It is understood that certain steps may be performed in an order different from what is shown. It is also understood that certain steps may be eliminated.

At step 300, the location of devices 120 (FIG. 1) may be determined, for example, by controller 120' based on information previously received from devices 120. For example, controller 120' (FIG. 1) may directly communicate with devices 120 to determine their locations. As another example, the location of devices 120 (FIG. 1) may be known from communication with communication system 150 and/or sever 140.

At step 302, a subset of devices 120 (FIG. 1) may be selected, for example by device selection/data acquisition module 240 (FIG. 2B) of controller 120'. For example, controller 120' (FIG. 1) may select one or more devices 120 based on a predetermined characteristic of the environment and the location of devices 120.

At step 304, sensor information and/or locally processed information may be received by controller 120' (FIG. 1) from the selected subset, for example, by device selection/data acquisition module 240 (FIG. 2B). For example, controller 120' (FIG. 1) may receive raw sensor information from respective sensor modules 202 (FIG. 2A) and/or locally processed information from respective local data analysis modules 204 (FIG. 2A). Controller 120' (FIG. 2B) may also acquire sensor information and/or locally processed information from its own sensor module 202 and local data analysis module 204. The information from at least one of the devices 120 may be received responsive to a confirmation indication from the respective device 120, to indicate an allowance by device 120 to release its respective information to the controller. For example, the confirmation indication may be provided manually by a user of the respective device 120, or may be provided automatically by the respective device 120, based on the privacy settings of the device 120.

At step 306, information received from the subset (as well as, optionally, from controller 120' (FIG. 1)) is combined to determine a characteristic of the environment, for example, by scene analysis module 242 (FIG. 2B) of controller 120'.

At step 308, it is determined whether the subset should be adjusted, for example, by device selection/data acquisition module 240 (FIG. 2B) of controller 120'. For example, the subset may be adjusted based on an event detected by a local data analysis module 204 (FIG. 2A) of one or more devices 120, the characteristic of the environment, any context from the characteristic, the location of devices 120 (FIG. 1) (e.g., position, orientation in space), demographics from the characteristic, any social-graph membership among devices 120, etc. For example, if one device 120 (FIG. 1) detects a gunshot, device 120' may expand the subset of devices 120 to additional devices (to triangulate the location of the gunshot) and/or to send a warning indication to all devices 120 in range.

If it is determined, at step 308, that the subset should be adjusted, step 308 proceeds to step 310. At step 310, selection of the devices in the subset may be adjusted and/or a configuration of selected devices of the subset may be adjusted, for example, by device selection/data acquisition module 240 (FIG. 2B). For example, different devices 120 (FIG. 1) may be switched on or off. As another example, different sensors of sensor modules 202 (FIG. 2A) may be configured to acquire sensor information.

If it is determined, at step 308, that the subset should not be adjusted, step 308 may proceed to step 304, to continually determine a characteristic of the environment.

Alternately, step 308 may proceed to step 312 (environmental monitoring), step 314 (localization and tracking), step 316 (topic monitoring), step 318 (triggering events) and/or step 320 (other monitoring and regulation). The characteristic of the environment may be used for a number of different applications, which are described further below.

Referring generally to FIG. 1, in an exemplary embodiment, a platform may be developed to enable users to develop applications that: harness a set of these devices 120; acquire signals from devices 120; switch subsets of devices 120 on or off (based on information about context, including position, orientation in space, social-graph membership, and demographics); process and analyze information obtained from sensors of devices 120; set triggers to enable or disable sensing, processing or analysis; and adapt system 100 to sensed, processed or analyzed information. The platform may allow individual devices 120, 120' to be customized and personalized to users (consumers) to mitigate, amplify or pass-through acoustic and other information to users based on acoustic and other information acquired from one or more devices.

Once such a platform is developed, applications may be developed for many of the scenarios and use-cases described herein. The platform may specify minimum hardware requirements, such as minimal sensor numbers and configuration, minimal onboard computing resources in terms of hardware and software, and an application programming interface (API) to allow developers to access all the features and resources available on the device.

An example platform specification may include: one or more microphones or a microphone array; one or more accelerometers typically to cover two or three axes of motion or orientation; a compass; an on-board GPS system; zero or more other sensors such as contact or non-contact temperature sensors; cameras with a minimal required resolution, with Bluetooth.RTM., Wi-Fi and other capabilities; software including classifiers to analyze speech, to analyze media including music, video, and still images; software to acquire environmental metrics and analyze them in various contexts such as urban vs. suburban, and residential vs. industrial; software to preprocess signals acquired to remove or reduce noise, filter the remaining signals to identify high value signals and to transmit them to a server 140 in a compressed form if desired; a database of sound signatures; and software to handle reactive mechanical tasks in response to sensor data—all with enough power to provide a realistic and acceptable user experience.

2 Example Use Cases

In this section, a number of example use cases are provided to illustrate how an exemplary system 100 (FIG. 1), described above, may be used in practice.

2.1 Environmental Monitoring A number of uses relate to monitoring an environment of a set of smartphones. In a public health monitoring example, the on-board audio processor may be configured detect occurrences of coughs, typically by the owner of the device or by other people in the proximity of the device. Such detection may use, for example, statistical spotting techniques (e.g., Hidden Markov Model (HMM) techniques, Gaussian Mixture Model (GMM) techniques) trained on a corpus of recordings of coughs know as a Universal Background Model. Communication of locally aggregated results, for example, a number of coughs per hour, may be uploaded to the central server 140 or device 120' on a schedule, or when the rate deviates from an expected or maximum value. In this way, the controller 120' (or server 140) may be able to identify local "hot spots" of coughing.

Other educational and public health uses may be possible with epidemiological applications of such systems. For example, pertussis (whooping cough) is a highly contagious disease and one of the leading causes of deaths world-wide that is preventable with the use of vaccines. Exemplary system 100 may be used to provide information to parents of children with coughs or with other symptoms such as asthmatic symptoms to help them decide when to seek medical help, and to provide epidemiological data about pertussis, asthma and related illnesses.

In some scenarios of such monitoring, only a limited subset of devices may be initially configured to perform the local processing needed to detect the coughs. However, when controller 120' determines that there is a possible hot spot of activity, controller 120' may enable further devices in the geographic proximity of the hot spot to gain further information about the extent of the situation. In some examples, the controller 120' may enable further devices based on a social proximity, for example, to account for the possible transmission of an illness to others that are close in a social sense. In addition to enabling further devices, the controller 120' may disable devices and control the overall monitoring set for the task.

In a variant, the system 100 may use sensed information to alert patients to asthmatic attacks in children, along with information on the child's environment at the onset of the attack, to enable them to ensure that prompt remedial or palliative action is taken.

In yet another variant, the system may be used to alert patients of breathing disorders such as sleep apnea. Sleep apnea is a disorder that is characterized by abnormal low breathing or abnormal pauses in breathing during sleep, often accompanied by snoring. Often the snorer is not aware that they snore or that they could have a life threating medical issue, and they suffer from fatigue, daytime sleepiness and other symptoms, often for years and years. Diagnosis often requires an overnight sleep study in a special lab set up with sensors. Knowledge about snoring and having a record of snoring behavior can help in the diagnosis and remediation of this condition. System 100 may be trained to recognize snoring, and to distinguish it from other kinds of similar noises, and help in detecting and recording snoring behavior to help people with breathing disorders identify their problems and seek appropriate help.

In another monitoring use case, the devices 120 may be used to monitor environmental sound levels (e.g., sound pressure level), for example, for workers in a factory workplace. Devices 120 of workers monitor the noise level and maintain a record, for example, cumulative durations of various ranges of noise level. This locally-determined information may be provided on regular or locally triggered basis, for example, if the noise level exceeds certain prescribed limits (e.g., an absolute limit, a limit for accumulated time above a prescribed sound pressure level, etc.). The controller 120' (or server 140) may query further devices 120 to determine the location of high noise levels, for example, based on locally logged detailed information that correlate noise level and location within the workplace. Also, other characteristics of environmental sound, for instance, related to the source of the sound may be detected. For example, a machine type (e.g., whistle, engine, press, saw, drill etc.) may be discriminated, for instance using pattern matching techniques (e.g., HMM, GMM techniques).

A similar sound-level monitoring may be used to track environmental sounds levels, for example, in particular restaurants, on particular streets, etc. and such monitoring may also identify time-of-day variation of such levels. Ornithologists may be interested in the ability to monitor the presence or absence of bird songs over time and space. Others might be interested in using sound arrays to monitor insect infestations. Exemplary system 100 may make it possible to compare treatment areas with controls to measure the effectiveness of proposed countermeasures. In some examples, if the device 120 is not connected to the communication system 150, information is logged, time stamped and stored in a non-volatile memory and then uploaded when the device 120 is once again connected or its memory is interrogated. This may be typical after an automobile accident or other fatal or non-fatal incidents.

If a large number of cars on the same highway suddenly decelerate at the same time, then the network could decide to issue a warning to cars a few miles behind the obstacle. In addition, the ability to measure traffic flow using an array of smartphones (equipped with communication networks and sensors such as accelerometers and microphones and GPS/location sensors) has the potential to improve traffic routing in the short term, and traffic planning in the long term. Many of the applications envisioned in the present invention may have both short-term and long-term benefits. Short-term benefits use networks with low latency (such as the radio stack), whereas long-term applications can make use of networks with longer latency (such as uploading information at the end of the day when the device is docked in a networked cradle).

In another monitoring use, phones may be enabled to "name that tune" in the environment, and both provide the owner to download that song to their device library and upload the location of the playing to the central controller, which monitors the aggregated presence of different songs. Consider a music festival with several stages, where different groups are playing. As the user walks around these stages, a network of systems may be continuously acquiring audio data, detecting and isolating, for instance, music, identifying the music and showing users the name of the piece being played, the album, the artistes playing etc. The system may provide a mechanism for users to purchase the music if it is of interest to them. There are stand-alone programs to identify music being played, but they require a single device to collect a good sample of music, send it to a server and then possibly identify the music. In contrast, by having a network of devices 120 collect data, data acquisition is more robust and distributed, and users are able to get their music identified faster.

Detection of particular music being played in the environment of devices may be aggregated to determine marketing related information. By monitoring what people hear as they go about their lives, the system may acquire considerable information about the media segment. The information captured on music played, the artiste/group being played, the volume of music purchased etc. is very valuable, especially when pivoted on various dimensions. In addition, in stores where music is sold, features such as the audio background and lingering behavior may also be valuable.

These devices may also be used to share information about what users listen to or see, or to find out what their friends are seeing or listening to. Currently users have to take the effort to tweet or post their music-playing or video-watching behavior. However, a few days of this can get tedious, and soon users may no longer post information on their listening or viewing habits. Exemplary devices 120 may automatically identify songs or TV programs, inform friends in the users' social graph or create virtual communities of users with similar listening or viewing interests.

2.2 Localization and Tracking

Some use cases take advantage of the multiple locations of the devices 120 to perform localization and/or tracking of audio sources. In one example, aircraft noise data may be obtained by having a "jet detector" implemented in the on-board audio processor of a set of devices 120. Upon detection of a loud jet noise, which is reported to the controller 120' (or server 140), other devices 120 in the proximity of the reporting device(s) 120 are enabled. Buffered time stamped audio and device location data is uploaded to the controller 120' (or server 140), where a triangulation approach may be used to determine a track of the detected audio source. Based on the track, further devices 120 may be enabled along the project track so that the audio source may continue to be tracked. If the source is lost (i.e., doesn't follow a predicted tract), more devices 120 over a larger area may be enabled to re-acquire the location of the audio source. In this way, an overall assessment of the audio tracks of loud aircraft may be determined based on the aggregated acquired audio data.

The selected set of devices 120 effectively acts as a configurable microphone mesh for acquiring audio data. In other examples, the devices 120 can act as a configurable accelerometer mesh for acquiring spatially and/or temporally distributed motion-related data.

Similar tracking information may be used, for example, to track sirens in a city. Such tracking may be used, for example, to predict traffic flow in a city that may be affected by an emergency.

Another type of localization may be used in near real-time or in an after-the-fact forensic mode. For example, the devices 120 may be carried by police officers or bystanders near the scene of a shooting. After detection of a gunshot event by one or more of the devices 120 (e.g., the officers' devices), the controller 120' (or server 140) may upload locally buffered audio from the officers' devices 120 or other devices 120 in the environment, and perform a localization of the source of the shooter's location. In a near real-time example, this information may be provided to the police officers to aid in their police duties. A similar type of arrangement may be used in a military situation in which audio is buffered at devices 120 carried by multiple soldiers, and the combined information may be used to estimate the direction of a sniper location.

Note that a central server 140 is not necessarily required. For example, devices 120 may locally exchange information to perform aggregated analysis, such as localization. In one such example, each device 120 may include a detector for an event of interest (e.g., gunshot), and upon detection of the event may pass the raw audio or a partially processed version of the audio (e.g., an intensity time profile) to nearby devices 120 (e.g., using ad hoc wireless communication), which perform local assessments of shooter direction based on the information they obtain.

In yet another scenario, these devices 120 may be used for adaptive crowd control. In situations with high traffic, whether vehicular or pedestrian traffic, these devices 120 may be configured as a mobile ad hoc network to estimate traffic flow from noise, with no requirement for any fixed or embedded sensors. Using the dynamically acquired traffic pattern information, the system 100 may broadcast instructions though the devices 120 or through other means to direct people through paths of lower traffic density, open up different gates or paths, or use sonification or acoustic visualization to alert users to high traffic versus low traffic paths.

A related idea is to create mobile sound-based security systems where the system 100 is able to quickly learn about ambient conditions and sound trends, and use this to signal situations away from normal conditions.

In another use case, these devices 120 may use sentiment detection and emotion detection to identify centroids of trouble in large crowds. A variant of this system 100 can be used to detect user dissatisfaction in their language, or in non-speech audio to alert management to, for example, open more counters in stores.

When users try to meet up with friends in large auditoria or sports stadia, it is often impossible to use mobile phones or to hear conversations on phones. The system 100 may use knowledge of users' social graphs to indicate the presence of friends using directional sonic visualization or sonification, with some variation in tone or volume as users approach their friends. Using the peer to peer architecture of the system 100 along with the knowledge in each device 120 about its neighboring devices 120 and their features, the system 100 can quickly and effectively determine the possible locations of friends. By utilizing the position information, and the orientation information acquired from the user's device 120, the system 100 can provide differential tones, volumes or other signals to indicate whether the user is moving towards or away from their friends (and whether they are pointed towards or away from their friends), and provide an indication about how far away they are. The precision of this indication may go up with the number of peer devices 120 contributing information to the system 100.

In another localization use case, a number of devices 120 may be enabled to sense audio, for example, for a group conference call. The locally acquired audio may be used to identify the location of the speaker, and to control which device 120 (or devices 120) are used to generate the audio for the call. For example, a device 120 closest to the person speaking, or the device 120 providing the highest signal quality or intelligibility, may be selected, thereby providing an improved audio quality.

In another localization use case, devices 120 may be tracked during a shopping trip, for example, in a grocery store or at a mall. The track taken by the user with corresponding audio or video information may be used to identify areas of customer focus and interest, and provide user-specific information, for example, promotional information related to purchase opportunities in the vicinity of the device 120.

After-the-fact analysis of a track may be used to correlate movement with actual purchases made, or to possible interest in various classes of items. For example, a relatively high time spent in the vicinity of a product type may indicate an interest in that product type. Users may be interested in opting in to having their path tracked in exchange for receiving promotions.

2.3 Topic Monitoring

In another use example, a device 120 may be enabled to monitor the owner's environment as they converse during the day, and as they listen to media broadcasts. Topic detection techniques, for instance, based on spotting topic-related keywords, may be used to assess topics of interest to the user. During the day, or in a periodic summary, the user is presented with collateral information related to the topics. For instance, if the user enters into a conversation about a particular topic, recent news or background material may be offered on the device 120. Such topic monitoring may also be useful to provide other targeted material to the user, for example, in the form of advertising that is relevant to the user's interests.

The configuration of other devices 120 may be adapted based on what is detected at the user's device 120. For example, other devices 120 in geographic or social proximity to the user's device 120 may be configured to detect the presence of similar topics. In this way, the other devices 120 may have a higher likelihood of correctly detecting the topics. Furthermore, the controller 120' or server 140 may be able to track the extent of interest in a topic.

Another topic-related monitoring use may be related to a third party requesting detection of audio signals, such as audio components of advertising to determine where these advertisements have been played. For example, an advertiser may have controller 120' or server 140 configure devices 120 to detect an advertisement, and then determine where the advertisement has been played and potentially heard.

In a related use case, the system 100 may use information garnered from the sensors of devices 120 and from other sources such as electronic program guides (EPG) to identify what programs users have been listening to or viewing, to get Nielsen-like viewership statistics or to acquire business intelligence. Current systems tend to rely on home systems or manually created diaries, both of which are prone to error. Using exemplary devices 120 and exemplary system 100 may allow for this monitoring to be done wherever the user is, and whatever media device they use, and to use information from user activity to distinguish active listening or viewing from, for instance, a TV playing to an empty room.

2.4 Triggering Events

Generally, use cases described above use various triggering events to begin local logging of audio and/or to initiate communication with the server 140, device 120' and/or other nearby devices 120. In addition to audio-based events (e.g., specific words, spoken topics, music, sounds, etc.), other events may trigger monitoring and/or communication. For instance, content of text communication (e.g., Short Message Service (SMS) messages) may initiate monitoring and/or configure what is to be searched for. Other data, such as accelerometer data, biometric data, and detection of a video image (such as change in luminance, etc.) that is available to the device may also be used in a trigger. For example, high acceleration may be associated with a vehicle accident or a fall, and this may initiate audio monitoring or communication with the server 140 (or device 120'), which may be able to determine if an accident has occurred based on the audio scene 130, in which case emergency help may be summoned.

The system 100 may also be used in the care of the elderly and the disabled. Currently senior citizens and the disabled can purchase a conventional device to signal when they need help, for example if they fall or feel dizzy. However, these conventional systems require the user to consciously make a decision and press a button on the device to ask for help. The problem is that there may be situations where the user cannot make the decision, may be too embarrassed to ask for help, may feel their problem is not critical enough to ask for help, or may not even be able to access the button to call for help. For instance when the user has a stroke or if they have a fall, it may be difficult for an elderly user to press the button. The system 100 described here may use data fusion ideas to combine speech and noise detection from one or more devices 120 along with other accelerometer data to detect calls for help, or sounds from falls, dropped objects, etc., distinguish between false alarms and real problems, and summon help when required as well. System 100 may also be able to turn on the speaker phone to have a dialog with the "help" side of the call.

In another form of triggering event, when a device 120 is removed from the direct acoustic environment, for example, by being put in a user's pocket, the change in audio signal characteristics may trigger a message to the controller 120' or server 140 to indicate that the device 120 is no longer available for acquiring audio based on a poor signal-to-noise ratio (SNR) operating environment. Similarly, when the device 120 is taken out of the pocket, it may again start monitoring the environment and/of notify the controller 120' (or server 140) that it is once again available. In addition, when the device is no longer obtaining adequate SNR, the device 120 may be able to enable other devices 120 within its proximity to acquire the signal and thus improve the overall SNR. In addition, many devices are now manufactured with multiple microphones (primarily used for beam forming) as to obtain an improved SNR for the user. As the user may often carry the device 120 in their pocket or purse, system 100 may be able to select which microphone in the device 120 is desirably enabled or what beam forming array would be best evoked to obtain a maximum SNR.

In some examples, vehicle texting is disabled by the system 100. By detecting an acceleration signature consistent with being in a moving vehicle and/or by picking up the type of sounds picked up while driving, the device 120 can detect road noise, the engine noise, wheel bearing noise, breaking noise All of these sounds may be used to either disable or enable the user from utilizing their device 120 for texting while the car is in motion. The device 120 may query its proximity and determine if other devices 120 were present within the body of the automobile. Assuming the answer were yes, further analysis may be used to provide limitations on the driver's device 120 from texting while still allowing the balance of the individuals to text. Some cars also disable or limit select navigational controls for safety reasons when the car is in motion. If the device 120 is able to detect a front seat passenger, the system may choose not to limit navigational controls.

In some examples, key word spotting obtained from in-situ conversations is aggregated from both the sender and recipient. During the course of normal telephone conversations, the device 120 may identify specific sounds, words, etc being uttered by both parties of a conversation. The system 100 may interrogate these sounds and provide the user with information either thru a graphical user interface (GUI), or audio based or text based feedback. As an example, assuming a call was about a trip to Paris, the device 120 could render information about promotional pricing on an airline to Paris.

One or more of these devices 120 may be used to identify trends in audio and other information acquired by these devices 120, for example using keyword spotting in audio streams. Keyword trends may be used to adaptively mediate or modify information consumed by users. In one scenario, information sources such as news media, search engines and similar information outlets may acquire information on trends from individual users or groups of users, and show different items to different users based on keyword trending. Specifically such a system 100 may choose topics users have been known to prefer.

Trending on non-speech audio may be used to identify patterns of people flow or vehicular flow. Aggregated logs of speech and non-speech audio may be used for a number of diverse applications, including identifying less noisy apartments or houses to rent or buy and areas of hotels or theater halls that may be better soundproofed. Longer term trending and identification of trends and periodic variations may be used for soundproofing or weatherproofing offices and residences.

2.5 Other Aspects and Uses

The ability to aggregate information over many smartphones can be provided with or without the cooperation of the carriers. It could be done, for example, with a third party application, which doesn't need the approval of a particular carrier and communicates via Wi-Fi or Bluetooth.RTM. In this way, information can be aggregated across phones serviced by multiple competing carriers.

In some exemplary embodiments of the system 100, the system 100 may trigger off key events such as rapid deceleration of several cars at the same time and place, sirens, keywords, etc. The ability to collect vast quantities of data may improve the triggering capability. Search companies are providing better search relevancy than ever before, largely because they are collecting more data than was possible before, the popularity of modern search engines. But with the exemplary system 100, it may become possible to collect even more data. If every phone were collecting audio data for an hour a day, the aggregate data resource would be much larger and much more valuable than the data collections currently collected by even the largest search companies.

In some exemplary embodiments of the system 100, if a device 120 in the system 100 may detect certain important keywords and phrases like "fire," then the system 100 may respond appropriately. The importance and urgency of a term depends both on the consequences of inaction as well as term weighting concepts that are well known in the field of Information Retrieval.

Similarly, if a system 100 hears an important term (such as a keyword like "fire" or a non-word like a cough or an event picked up on some other sensor of device 120 such as a rapid deceleration), then the system may turn on numerous other nearby sensors in the array to confirm the event, to improve the signal to noise ratio and/or to localize the event in time and space.

In some uses, trending analysis may use the large amount of data available through the system 100. Consider the cough example mentioned above. Aggregations of coughs over time and space may provide tracking of health over time and space. The approach is similar some approaches to prediction of the flu based on queries where they showed that they could predict flu a couple of weeks faster than the Centers for Disease Control and Prevention (CDC). But the proposed cough metric should have even better resolution over time and space since it is based on a larger quantity of sensed data.

Collection of large amounts of sensed data provides a way to systematically predict (e.g., according to a statistical model) sequences or sets of sensed events of other information. Such prediction may effectively be exploited based on principles related to Shannon's Noisy Channel Model, for example, to improve transmission capacity for such events. For example, such data can allow one to create a better "language model" for events, which will do a better job of predicting what sounds to expect to hear (the prior for the noisy channel model) as well as sounds that are anonymous (triggers that should sound alarms and start recording).

In some examples, workplace monitoring (and monitoring of the environment) may be enabled by the system 100. The system 100 may effectively provide "smartdust" on smartphones, which is able to monitor workplaces for health issues by measuring acoustical events like coughs. Moreover, in some uses, the system 100 may sense correlates of stress such as noise. Some call centers, for example, have more stress related illnesses because the call volume has relatively large numbers of unhappy customers. It may be possible to predict risk of certain types of illnesses well before symptoms develop, both at work as well as elsewhere.

An ad hoc network of devices 120 may be used to fine-tune a number of features. Consider concert-hall acoustics, for instance. Concert halls are typically tuned for the major uses of their space. For example, a symphony hall may be tuned especially for a large group of artistes and their instruments, and may not be as well suited to, for example, solo vocalists. Sound quality in a hall is also dependent on the size of the audience, their ambient noise characteristics etc. The network of system 100 may enable data to be acquired from a large number of devices 120 in the audience, so that the hall management can adapt to the ambient noise levels and fine-tune sound levels for any performance, with any number of performers and instruments, and with different audiences.

The ad hoc network can also be used for monitoring and regulatory purposes. Sound pressure levels or similar measures of rock concerts, gym classes and other potentially noisy environments may be monitored against safe listening levels, and infractions reported to the appropriate management or regulatory agency.

A similar scheme may be used to fine-tune the temperature in large auditoria, rooms or halls, based on data acquired from a number of devices 120 and individual sensors in that space. Large spaces have their own airflow and heating and cooling patterns, based on placement of air ducts, windows, doors and other openings. Heating and cooling is typically based on measuring temperature in one and occasionally more sensing locations. If the sensor is near a sunny window or a draft caused by a constantly open door, the temperature in that space can be unsatisfactory. By measuring temperature in several locations using a set of devices 120 as described in this invention, it will be possible to have finer, more localized control of temperature.

Some exemplary embodiments of the system 100 may make predictions based on a small sample of "opt ins." The system 100 (e.g., "cloud") may be equipped with appropriate logic to determine how to make appropriate inferences based on information gathered from those phones 120 that choose to opt into the system 100. Many of these inferences are relatively straightforward, though care may need to be taken to account for the fact that the sample is not a random sample. The set of people that own a smartphone and choose to participate will be skewed toward certain demographics, at least in the near term.

3 Backup Communication Uses

In some versions of the system, the mesh-like features of the set of personal devices 120 may be exploited. Cell phones may be viewed as relatively passive (receive only) devices, but there are times, such as during an emergency, where it could be desirable to be able to deploy an active communication network very quickly as an overlay to more traditional telephone and internet networks.

During an emergency such as a man-made event like September 11 or a natural disaster such as a major hurricane, it is possible that parts of key communication infrastructures could be down.

There was a time when telecommunication networks were much more protected than they are these days. The telephone network used to be more reliable than the power grid. Central offices are typically backed up with batteries and generators (and submarine doors in places like New Orleans that are subject to flooding). Plain old telephone service (POTS) handsets used to be powered from the central office, so the service could stay up even if the standard power grid was down.

These days, most handsets sold in popular stores depend on the power grid. Most phones have lots of features and a power cord. Some have battery backup, but there is little incentive to replace the battery. Soon, the battery backup feature may be a thing of the past because many people aren't willing to pay for such features. Engineers like to design bridges for the hundred years' flood, but it is hard to persuade customers to pay for features they probably won't use. Given these realities, it is desirable to develop a way to deploy a backup network just-in-time. Unlike batteries and generators, which are expensive whether we use them or not, a backup network based on phones typically won't cost the public much if any additional capital, because most of the equipment is already in place.

Key features of a backup network:

1. Two-way communication: Telephone receivers normally receive but they can also be used to store and forward information. Thus for example, if a phone was on a mobile platform (say in a pocket or in a car), then the phone could be used in sneakernet mode to store a signal in one place and repeat it from another place.

2. Damage Assessment (the ability to determine quickly and easily what is working and what is not): During September 11, there were many outages (e.g., fiber cuts under #7 World Trade Center, cell towers on the rooftops, switches under both #1 and #2 World Trade Center, police and fire radio communication in certain places), but some things were working (e.g., cell towers in New Jersey, BlackBerry™ email, systems based on satellites). A key requirement is to determine what is working and what is not, and to communicate workarounds to those that need them. An array of cell phones in a multitude of pockets and cars could determine fairly quickly what is working and what is not. Hopefully, some of these devices may be connected to something that is working (such as a satellite) or would eventually move out of the affected area so enough of them could report an accurate and timely damage assessment picture back to the cloud. Using this information, both digital and real world traffic may be adaptively rerouted.

3. Workarounds: Municipal vehicles such as buses have batteries and generators. Soon, such vehicles may also have Wi-Fi that is connected to satellites. The cloud could direct such resources where they are needed most.

An acoustical array, such as what is described herein, may also be used in damage assessment. For example, the acoustical array may determine both whether there is too much noise (e.g., explosions) as well as too little noise (e.g., absence of human activity), aggregated over time and space.

4 Authorization and Privacy

In some exemplary embodiments of the system 100, privacy considerations may be addressed using one or more features, which may include the following. First, monitoring may be enabled on a device 120 only if the user explicitly "opts in" to permit particular monitoring options. A reason that a user may accept such monitoring is that he, in return, obtains information that is valuable to him, for example, by being provided more relevant search results or other information. Another feature relates to encryption of the monitored information. For example, audio may be encrypted in a manner than prevents interception during uploading and/or processing by a controller 120' or server 140. Furthermore, in systems 100 in which multiple central controllers are used (e.g., one controller 120' or server 140 per cellular telephone carrier), the user may explicitly permit sharing between or among controllers.

In some examples, devices 120 may have features that inhibit collection of audio environment data. Such features may be mechanical (for example, mechanically preventing audio pickup with a shutter mechanism) or can be electronic (for example, with an electronic slider switch on the device).

In some examples, sensors can be selectively turned on or off both at the edge of the network (in the smartphone), as well as in the network (in the cloud), as well as elsewhere. For example, the operator of a movie theatre may have the ability to turn off speakers that would annoy others in the movie theatre, and similarly the operator of an airplane should have the ability to turn off communication features that could jeopardize the safety of fellow passengers. Moreover, after an incident, such as a plane accident, the authorities should have the ability to probe (via a wired or wireless interface to the memory of the phone-could be non-volatile) the smartphones on the plane for information that could be helpful in the investigation. In other words, the array of smartphones on the plane could serve as a kind of "black box" to prevent similar such incidents in the future.

However, privacy is also important in at least some versions of the system 100. In some exemplary embodiments, the owner of the smartphone should have the ability to pull the curtain with confidence that the phone is not invading the user's privacy, even if the phone has been taken over by a virus. When the curtain is pulled, the user wants to be sure that the phone is not recording information that could be embarrassing or self-incriminating. The phone should not be recording information that could be subject to subpoena or a court order such as discovery. The user should have the ability to opt out in a way that cannot be overridden by the owner of the network, government authority, or anyone else (such as a malicious hacker). For example, privacy may be implemented by a switch, as described further below.

Feature interaction can be a tricky problem in a communication network. While it is desirable that many parties have the ability to turn on and off certain features in certain ways, as discussed above, it is also important that it be clear to all parties what happens when different parties issue commands that may conflict with one another in complicated and unanticipated ways.

In particular, in at least some exemplary embodiments of the system, the owner of the phone ought to be in charge. In such embodiments, the owner may have the ability to physically disconnect the sensors in a way that cannot be overruled by any other party. One such method may include a physical switch that would disconnect the sensors in a way that the user can verify by visual inspection of the phone. The physical switch may be operated manually by the user and cannot be overridden remotely under software control.

In addition to the physical switch, there may also be a software controlled switch that may empower authorized parties to turn on and off features such as recording of sensors, recognizing keywords and uploading appropriate information to the cloud where inferences can be made that aggregate over space and time. Policies may eventually be determined regarding who is allowed to do what, and what is appropriate and what is not.

5 Other Devices

As introduced above, the exemplary approaches described above are not limited to smartphones. For example, in-vehicle systems (e.g., navigation devices), media devices (e.g., televisions, set-top boxes, desktop computers, laptop computers), and other fixed or mobile devices may be used in similar ways. For example, in the case of an in-vehicle navigation system, an in-vehicle conversation may be monitored and information about a location (e.g., a restaurant) that is being discussed may be provided on the device's display.

Another type of device that may be used in such a system is an earpiece that provides audio input and output for a telephone (device). An advantage of monitoring with the earpiece is that it is exposed to the acoustic environment even when the associated phone is not exposed to the environment, for example, when the phone is in a user's pocket, thereby providing an improved signal-to-noise ratio (SNR). Another embodiment may have the entire mobile communication (cell phone) being integrated into the earpiece.

Another type of device 120 that may be used in such a system 100 is a hearing aid. The hearing aid may allow the entire feature set thus described in herein to be made practical. The advantage of this is data which could be mined from this age population is thought to be very different for the generation of users who typically use headphones for their communication activities.

Use of earpieces as described above can be thought of as ownership or control of the "last inch," which is similar to the ownership of the "last mile," which has been strategically important in the telephone business. The same dynamic underlies the debate over net neutrality. So too, ownership over the last inch will become strategically important in the war over eyes and ears.

The web is currently about eyeballs and mouse clicks, but soon the war will move to a struggle for access to ears as well as eyes. The hearing aid or earpiece could be viewed as a chief of staff. It gets to decide what the user hears and what the user doesn't hear. The hearing aid could give the wife preferred access. It could also block spam, and filter out unwanted commercials. Alternatively, the hearing aid or earpiece could run an auction similar to a paid search, where the hearing aid is a market maker that attempts to find an equilibrium between the need of the user for relevance and utility to the advertiser.

These auctions typically use a Vickrey auction to encourage advertisers to bid their true utility. If the user chooses to follow up on an ad (with a mouse click), then the advertiser pays the second highest bid. The hearing aid or earpiece could work in a similar way though, perhaps, instead of clicking on an ad, it might be easier for the user to participate by some other means such as a spoken command.

Although the invention has been described in terms of systems and methods for processing information from a plurality of distributed devices, it is contemplated that one or more steps and/or components may be implemented in software for use with microprocessors/general purpose computers (not shown). In this embodiment, one or more of the functions of the various components and/or steps described above may be implemented in software that controls a computer. The software may be embodied in non-transitory tangible computer readable media (such as, by way of non-limiting example, a magnetic disk, optical disk, flash memory, hard drive, etc.) for execution by the computer.

For example, some of the software may include instructions for execution at the personal devices 120 and device 120'. This software may be stored on a non-transitory tangible computer readable medium at a central location, for example, at a server 140 for distribution to the devices 120, 120', may be transferred over a digital communication medium, and/or stored in a machine readable medium at the devices 120, 120' (e.g., as downloaded applications/applets). Some of the software may be hosted at central servers 140 (e.g., in a distributed "cloud" of processors) and made accessible by storing it on non-transitory tangible computer-readable media for execution on processors of the servers 140.

Although the invention is illustrated and described herein with reference to specific embodiments, the invention is not intended to be limited to the details shown. Rather, various modifications may be made in the details within the scope and range of equivalents of the claims and without departing from the invention.

I claim:

1. A system comprising:
a device among a plurality of acoustic devices; wherein the device is configured as a controller, wherein the controller is configured to perform operations comprising:
selecting a subset of acoustic devices from among the plurality of acoustic devices for acquiring sensor acoustic data, wherein the subset of acoustic devices are configured to interchange device information and data over a communication link;
receiving a first set of sensor acoustic data from a first acoustic device of the selected subset of acoustic devices;
receiving a second set of sensor acoustic data from a second acoustic device of the selected subset of acoustic devices; and
analyzing at least one of the first set of sensor acoustic data or the second set of sensor acoustic data or a combination of both to identify if speech is present.

2. The system according to claim 1, wherein the operations further comprise:
analyzing the speech for a keyword.

3. The system of claim 2, wherein the first set of sensor acoustic data and the second set of sensor acoustic data are received based on a triggering event.

4. The system of claim 3, wherein the operations further comprise:
determining a direction of measurement of at least one device of the subset of devices.

5. The system of claim 1, wherein the operations further comprise:
selecting the subset of devices based on geographic proximity to a user.

6. The system of claim 2, wherein the operations further comprise:
activating a sensor based upon the keyword.

7. The system of claim 1, wherein the operations further comprise:
generating an alert signal based upon an analysis of at least one of the first set of acoustic sensor data or the second set of acoustic data or a combination of both.

8. The system of claim 1, wherein the operations further comprise:
analyzing at least one of the first set of acoustic sensor data or the second set of acoustic sensor data or a combination of both for animal sounds.

9. The system of claim 1, wherein the operations further comprise:
determining the locations of each of the selected subset of acoustic devices.

10. The system of claim 2, wherein the operations further comprise:
determining which of the selected subset of acoustic devices is the closest acoustic device to a user that uttered the keyword.

11. The system of claim 10, where the operations further comprise:
determining a voice command from the keyword; and
sending the voice command to the closest acoustic device.

* * * * *